United States Patent
Kwon et al.

(10) Patent No.: US 12,121,315 B2
(45) Date of Patent: Oct. 22, 2024

(54) METHOD OF DETERMINING HYSTERESIS OF SURGICAL ROBOT, METHOD OF COMPENSATING FOR THE SAME, AND ENDOSCOPIC SURGICAL APPARATUS

(71) Applicants: Korea Advanced Institute of Science and Technology, Daejeon (KR); ROEN Surgical, Inc., Daejeon (KR)

(72) Inventors: Dong Soo Kwon, Daejeon (KR); Dong Hoon Baek, Daejeon (KR); Ju Hwan Seo, Daejeon (KR); Joon Hwan Kim, Daejeon (KR); Jeong Do Ahn, Daejeon (KR); Han Soul Kim, Daejeon (KR); Jae Min You, Daejeon (KR)

(73) Assignees: KOREA ADVANCED INSTITUTE OF SCIENCE AND TECHNOLOGY, Daejeon (KR); ROEN Surgical, Inc., Daejeon (KR)

( * ) Notice: Subject to any disclaimer, the term of this patent is extended or adjusted under 35 U.S.C. 154(b) by 863 days.

(21) Appl. No.: 17/277,159

(22) PCT Filed: Jan. 17, 2020

(86) PCT No.: PCT/KR2020/000862
§ 371 (c)(1),
(2) Date: Mar. 17, 2021

(87) PCT Pub. No.: WO2021/145490
PCT Pub. Date: Jul. 22, 2021

(65) Prior Publication Data
US 2022/0110703 A1     Apr. 14, 2022

(30) Foreign Application Priority Data
Jan. 17, 2020   (KR) .................. 10-2020-0006523

(51) Int. Cl.
*A61B 34/00* (2016.01)
*A61B 1/00* (2006.01)
(Continued)

(52) U.S. Cl.
CPC .......... *A61B 34/71* (2016.02); *A61B 1/00006* (2013.01); *A61B 1/00039* (2013.01);
(Continued)

(58) Field of Classification Search
CPC .... A61B 34/71; A61B 1/00006; G06N 3/045; G06N 3/08
See application file for complete search history.

(56) References Cited

U.S. PATENT DOCUMENTS

2007/0287992 A1* 12/2007 Diolaiti .................. A61B 34/71
   606/1
2010/0256558 A1* 10/2010 Olson .................... A61B 34/77
   604/95.01
(Continued)

FOREIGN PATENT DOCUMENTS

JP    2014104528 A    6/2014
JP    2015160278 A    9/2015
(Continued)

OTHER PUBLICATIONS

International Search Report related to International Application No. PCT/KR2020/000862 report dated Oct. 14, 2020.
(Continued)

*Primary Examiner* — Jonathan L Sample
*Assistant Examiner* — Mohammed Yousef Abuelhawa
(74) *Attorney, Agent, or Firm* — JCIPRNET (57) ABSTRACT

A method of determining hysteresis according to an example embodiment may include capturing a real-time image of the surgical robot driven according to a drive input, and measuring a drive angle of the surgical robot by comparing the
(Continued)

real-time image to a previously rendered image data set of the surgical robot, and calculating a difference between the drive input and the measured drive angle.

19 Claims, 10 Drawing Sheets

(51) Int. Cl.
  *A61B 1/018* (2006.01)
  *A61B 1/05* (2006.01)
  *A61B 34/30* (2016.01)
  *G06N 3/02* (2006.01)

(52) U.S. Cl.
  CPC ............... *A61B 1/018* (2013.01); *A61B 1/05* (2013.01); *A61B 34/30* (2016.02); *A61B 34/74* (2016.02); *A61B 34/76* (2016.02); *G06N 3/02* (2013.01); *A61B 2034/301* (2016.02)

(56) References Cited

U.S. PATENT DOCUMENTS

| | | | |
|---|---|---|---|
| 2017/0252114 A1* | 9/2017 | Crawford | A61B 17/1757 |
| 2018/0243897 A1* | 8/2018 | Hashimoto | B25J 9/1612 |
| 2019/0142520 A1* | 5/2019 | VanDyken | A61B 34/20 606/1 |
| 2019/0282123 A1* | 9/2019 | Crawford | A61B 5/062 |
| 2019/0327394 A1* | 10/2019 | Ramirez Luna | H04N 23/51 |

FOREIGN PATENT DOCUMENTS

| | | |
|---|---|---|
| KR | 20140011433 A | 1/2014 |
| KR | 20190094488 A | 8/2019 |

OTHER PUBLICATIONS

Baek, Donghoon et al. "Hysteresis Compensator with Learning-based Pose Estimation for a Flexible Endoscopic Surgery Robot", 2019 IEEE/RSJ International Conference on Intelligent Robots and Systems (IROS), Macau, China Nov. 4-8, 2019, pp. 2983-2989.

Do, T.N. et al. "Hysteresis modeling and position control of tendon-sheath mechanism in flexible endoscopic systems" Mechatronics, 2014, 24, 12-22.

Baek, Donghoon et al. "Image-based hysteresis compensator for a flexible endoscopic surgery robot", 2019 16$^{th}$ International Conference on Ubiquitous Robots (UR), Jeju, Korea, Jun. 24-24, 2019, pp. 299-305.

Baek Donghoon et al., "3D CAD Model-based pose estimation for flexible surgery robot using Siamese Convolutional Neural Network", Korea Advanced Institute of Science and Technology, Journal of the 14h Korea Robotics Conference, Jan. 20-23, 2019.

Dong-Hoon et al. "Hysteresis Compensator Using Learning-Bases Hybrid Position Estimation Method for Flexible Surgical Robot" The 10$^{th}$ Korean Society of Medical Robotics Conference, Aug. 31, 2019.

* cited by examiner

METHOD OF DETERMINING HYSTERESIS OF SURGICAL ROBOT, METHOD OF COMPENSATING FOR THE SAME, AND ENDOSCOPIC SURGICAL APPARATUS

CROSS-REFERENCE TO RELATED APPLICATION

This application is a 35 USC § 371 US National Stage filing of International Application No. PCT/KR2020/000862 filed on Jan. 17, 2020, and claims priority under the Paris Convention to South Korean Patent Application No. 10-20-0006523 filed on Jan. 17, 2020.

TECHNICAL FIELD

The following description relates to a method of determining hysteresis of a surgical robot, a method of compensating for the same, and an endoscopic surgical apparatus.

BACKGROUND ART

When a flexible surgical robot is used to perform surgery and examinations on digestive organs such as the stomach, large intestine, and the like, the sheath, which is a flexible part, of the flexible surgical robot, has various shapes due to the organs with various curves in a human body, which causes unpredictable hysteresis and makes it difficult to compensate for the same.

Hysteresis compensation algorithms are largely divided into two types: one is an offline method of compensating for hysteresis using already known information (a priori), and the other is a feedback-type online compensation method of utilizing a sensor.

The offline method includes a method of using a hysteresis model, a method of using a new kinematic model through training, or a method of reducing friction between the sheath and wires by using oscillation. However, these methods had issues in being unable to cope with changes in the characteristics of hysteresis, such as changes in the configuration of the sheath.

The online method representatively includes a method of using an electromagnetic sensor and a method of using a camera. The former is difficult to apply to actual surgery due to an issue in sterilization, and the latter uses "markers" that are mostly easy to be occluded by surgical secretions and thus has an issue in an appropriate compensation performance cannot be expected when the markers are occluded by surgical secretions.

The above description has been possessed or acquired by the inventor(s) in the course of conceiving the present invention and is not necessarily an art publicly known before the present application is filed.

DISCLOSURE OF INVENTION

Technical Goals

An aspect provides a method of determining a hysteresis of a surgical robot, a method of compensating for the same, and an endoscopic surgical apparatus.

Technical Solutions

According to an aspect, there is provided a method of determining hysteresis of a surgical robot according to a drive input, the method including capturing a real-time image of the surgical robot driven according to a drive input, and measuring a drive angle of the surgical robot by comparing the real-time image to a previously rendered image data set of the surgical robot, and calculating a difference between the drive input and the measured drive angle.

The method may further include, before the capturing of the real-time image of the surgical robot, generating a hysteresis evaluation model for a surgical robot based on similarities between (i) an actual image of the surgical robot and (ii) images rendered by driving a virtual surgical robot on a simulation that models the surgical robot based on a kinetic model.

The generating of the hysteresis evaluation model may include extracting a first feature vector by inputting rendered image data, which are a set of the rendered images, into a first neural network model, extracting a second feature vector by inputting actual image data of the surgical robot driven according to a drive input into a second neural network model, and training the first neural network model and the second neural network model by supervised learning, based on a difference in relative magnitudes of respective drive inputs of the rendered images and the actual image and on a difference in relative magnitudes between the first feature vector and the second feature vector.

The first feature vector and the second feature vector may have the same number of dimensions, and the training may include training the first neural network model and the second neural network model such that a norm size between the first feature vector and the second feature vector decreases as the respective drive inputs of the rendered images and the actual image are more similar to each other.

The surgical robot may include a proximal joint part and a distal joint part that have different rotation axes are articulated and driven, the drive inputs may include a drive angle displacement of the proximal joint part and a drive angle displacement of the distal joint part, and the generating of the hysteresis evaluation model may include generating at least two hysteresis evaluation models, for each interval of the drive angle displacement of any one of the proximal joint part and the distal joint part.

The generating of the hysteresis evaluation model may include generating at least two hysteresis evaluation models, for each interval of the drive angle displacement of the proximal joint part.

The generating of the hysteresis evaluation model may further include preprocessing the actual image by separating and removing a background image except for the surgical robot from the actual image.

The calculating of the difference may include extracting a real-time feature vector by inputting the real-time image into the second neural network model, retrieving a rendered image having the first feature vector most similar to the real-time feature vector, and determining the measured drive angle based on a drive input of the retrieved rendered image.

The retrieving of the rendered image may include indexing using a binary tree structure having the number of dimensions the same as the number of dimensions of the first feature vector.

The calculating of the difference may further include preprocessing the real-time image by separating and removing a background image except for the surgical robot from the real-time image.

The preprocessing may further include adjusting a scale of the real-time image based on a distance from a camera capturing the real-time image of the surgical robot to a proximal joint part of the surgical robot.

According to an aspect, there is provided a method of compensating for hysteresis of a surgical robot according to a drive input, the method including capturing a real-time image of the surgical robot driven according to a drive input, measuring a drive angle of the surgical robot by comparing the real-time image to a previously rendered image data set of the surgical robot, and determining hysteresis of the surgical robot by calculating a difference between the drive input and the measured drive angle, and compensating for the drive input based on the determined hysteresis.

The compensating may include compensating for the drive input with feedback control based on the difference between the drive input and the measured drive angle.

According to an aspect, there is provided an endoscopic surgical apparatus including a tube, a surgical robot received in the tube, the surgical robot having a drive shaft with one or more degrees of freedom, an endoscopy camera configured to capture the surgical robot at an end of the tube, a driver configured to drive the surgical robot, a controller configured to control the drive of the surgical robot by controlling the driver, and a drive input part configured to receive a drive input from a user, wherein the controller may include at least one processor configured to compensate for hysteresis of the surgical robot based on the drive input and a real-time image captured by the endoscopy camera.

The controller may include a hysteresis evaluation model for a surgical robot based on similarities between an actual image of the surgical robot and images rendered by driving a virtual surgical robot on a simulation that models the surgical robot based on a kinetic model.

The hysteresis evaluation model for the surgical robot may include a first neural network model configured to receive the rendered images and output a first feature vector of a plurality of dimensions, a second neural network model configured to receive the actual image of the surgical robot and output a second feature vector having the same number of dimensions as the first feature vector, and a supervised learning model configured to train the first neural network model and the second neural network model by supervised learning, such that a difference in relative magnitudes of respective drive inputs of the rendered images and the actual image is proportional to a difference in relative magnitudes between the first feature vector and the second feature vector.

The hysteresis evaluation model for the surgical robot may further include an index part configured to store first feature vectors extracted respectively for the rendered images in a binary tree structure having the number of dimensions the same as the number of dimensions of the first feature vector.

The surgical robot may include a proximal joint part and a distal joint part that have different rotation axes are articulated and driven, the drive inputs may include a drive angle displacement of the proximal joint part and a drive angle displacement of the distal joint part, and the hysteresis evaluation model may be generated as at least two different models, for each interval of a drive angle displacement of any one of the proximal joint part and the distal joint part.

The controller may be configured to extract a real-time feature vector by inputting a real-time image of the surgical robot into the second neural network model, and determine a drive error according to the drive input based on a rendered image having the first feature vector most similar to the real-time feature vector.

The controller may further include a drive compensator configured to compensate for the drive of the driver based on a size of the drive error evaluated according to the drive input.

The drive compensator may be configured to compensate for the drive input with feedback control based on the size of the drive error.

Effects

According to example embodiments, a method of compensating for hysteresis and an endoscopic surgical apparatus including the same may reduce hysteresis of a surgical tool with respect to various structures of a sheath, and improve the accuracy of controlling the surgical tool in application to surgery on a digestive organ such as the stomach, large intestine, or the like.

According to example embodiments, a method of compensating for hysteresis and an endoscopic surgical apparatus including the same may use images captured by an existing endoscopy camera, thereby excluding separate additional elements and an issue in sterilization accordingly.

BEST MODE FOR CARRYING OUT THE INVENTION

Hereinafter, example embodiments of the present disclosure will be described with reference to the accompanying drawings. Regarding the reference numerals assigned to the components in the drawings, it should be noted that the same components will be designated by the same reference numerals, wherever possible, even though they are shown in different drawings. Also, in the description of the example embodiments, detailed description of well-known related structures or functions will be omitted when it is deemed that such description will cause ambiguous interpretation of the present disclosure.

Also, in the description of the components, terms such as first, second, A, B, (a), (b) or the like may be used herein when describing components of the present disclosure. These terms are used only for the purpose of discriminating one constituent element from another constituent element, and the nature, the sequences, or the orders of the constituent elements are not limited by the terms. When one constituent element is described as being "connected", "coupled", or "attached" to another constituent element, it should be understood that one constituent element can be connected or attached directly to another constituent element, and an intervening constituent element can also be "connected", "coupled", or "attached" to the constituent elements.

The same name may be used to describe an element included in the example embodiments described above and an element having a common function. Unless otherwise mentioned, the descriptions on the example embodiments may be applicable to the following example embodiments and thus, duplicated descriptions will be omitted for conciseness.

Figure 1:
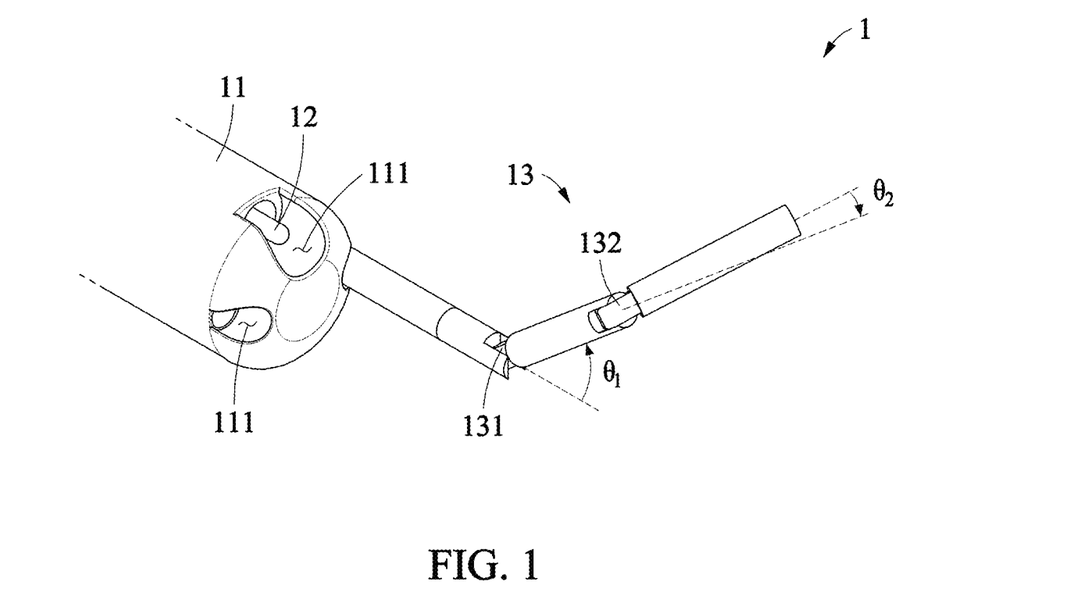
FIG. 1 is a perspective view illustrating an endoscopic surgical apparatus according to an example embodiment.
Figure 2:
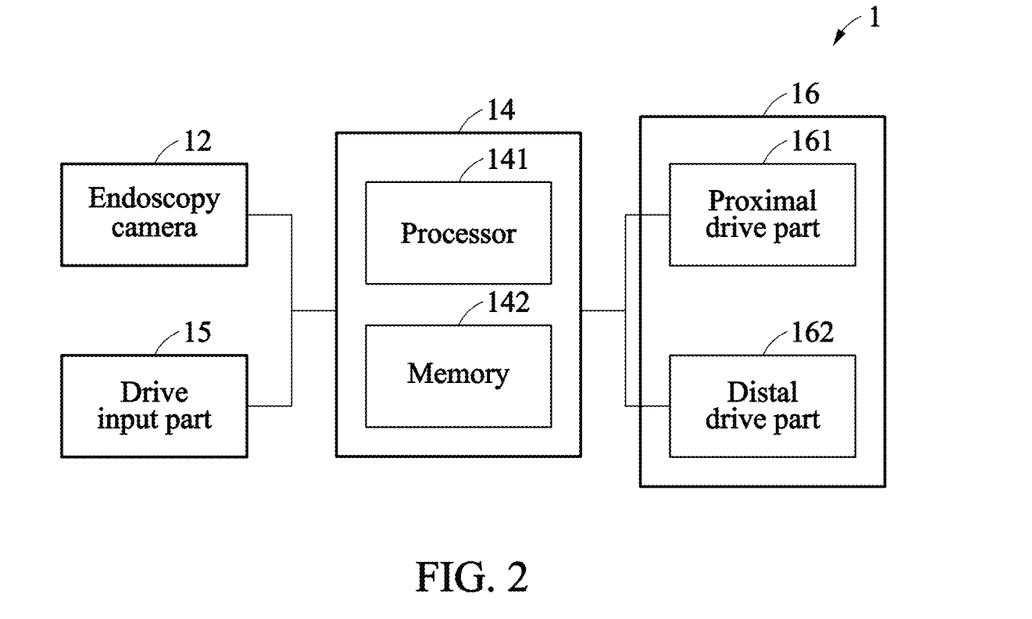
FIG. 2 is a block diagram illustrating an endoscopic surgical apparatus according to an example embodiment.
Figure 3:
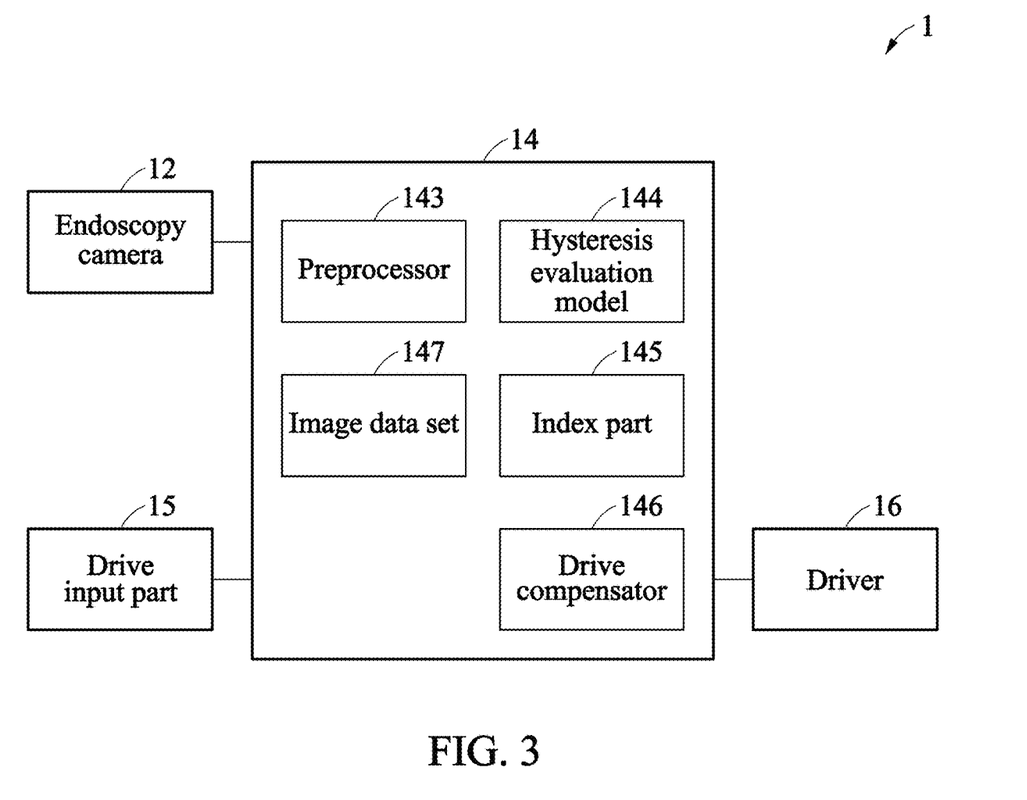
FIG. 3 is a block diagram illustrating a configuration of a controller in an endoscopic surgical apparatus according to an example embodiment.
Figure 4:
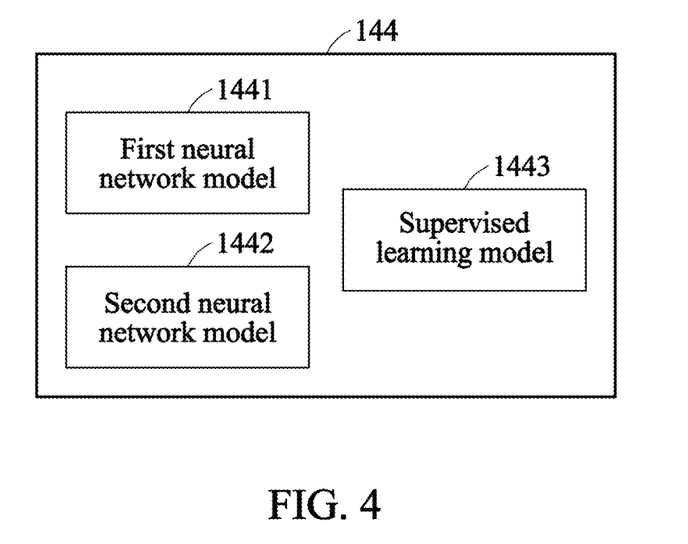
FIG. 4 is a block diagram illustrating a hysteresis evaluation model according to an example embodiment.
Figure 5:
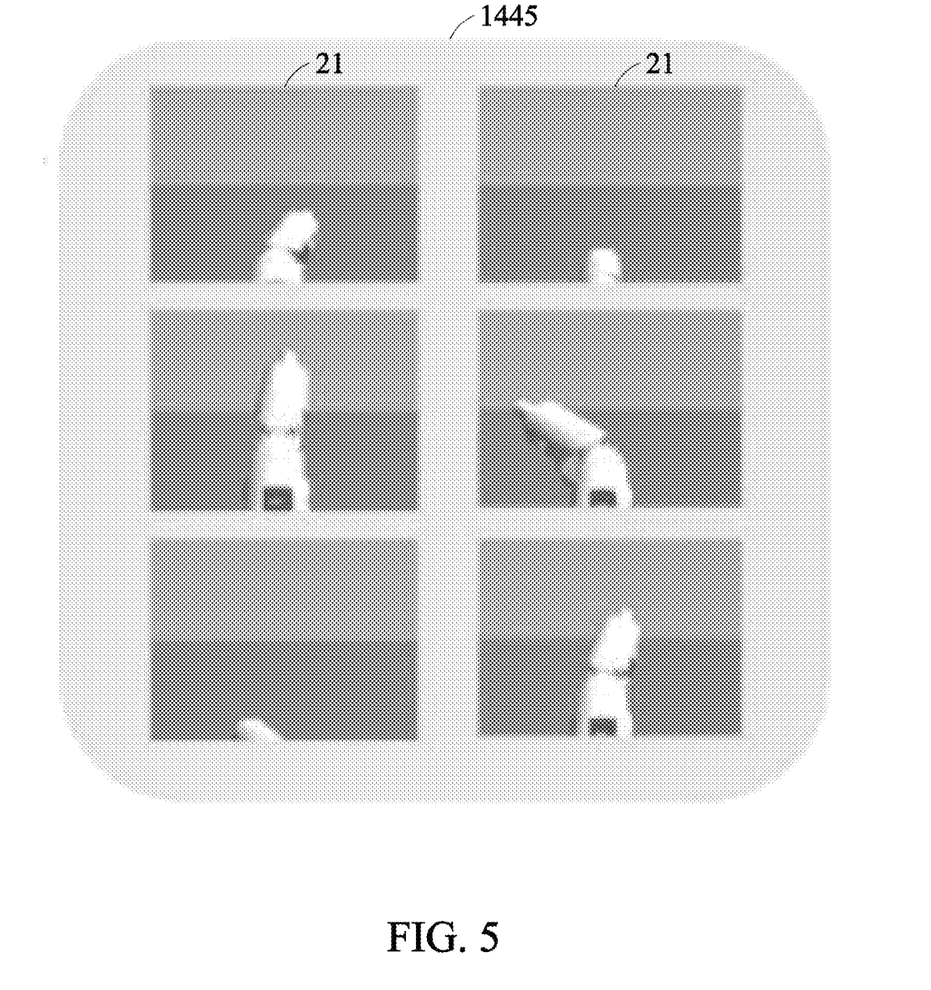
FIG. 5 illustrates a data set of previously rendered images of a surgical robot according to an example embodiment.

FIG. 1 is a perspective view illustrating an endoscopic surgical apparatus according to an example embodiment, FIG. 2 is a block diagram illustrating the endoscopic surgical apparatus according to an example embodiment, FIG. 3 is a block diagram illustrating a configuration of a controller in the endoscopic surgical apparatus according to an example embodiment, FIG. 4 is a block diagram illustrating a hysteresis evaluation model according to an example embodiment, and FIG. 5 illustrates a data set of previously rendered images of a surgical robot according to an example embodiment.

Referring to FIGS. 1 to 5, an endoscopic surgical apparatus 1 may be inserted into a body to perform surgical treatments and capture images at the same time, determine hysteresis according to a drive input of a surgical robot 13 based on an image acquired by capturing the surgical robot 13, and compensate for the drive input through this, thereby improving the control accuracy.

The endoscopic surgical apparatus 1 may include a tube 11 to be inserted into a body, the surgical robot 13 received in the tube 11, the surgical robot 13 to be driven with one or more degrees of freedom, an endoscopy camera 12 configured to capture the surgical robot 13 at an end of the tube 11, a driver 16 configured to drive the surgical robot 13, a controller 14 configured to control the drive of the surgical robot 13, and a drive input part 15 configured to receive a drive input from a user.

The tube 11 may be a flexible tubular member to be inserted into a body. For example, the tube 11 may include at least one channel 111 formed therein along the longitudinal direction to guide the surgical robot 13, the endoscopy camera 12, or other surgical tools to the end of the tube 11.

The surgical robot 13 may protrude out of the end of the tube 11 through the channel 111 and be driven by an input or manipulation of a user for surgical treatments.

The surgical robot 13 may be driven with one or more degrees of freedom. For example, as shown in FIG. 1, the surgical robot 13 may include two joint parts 131 and 132 that are articulated and driven in different directions, wherein the joint parts 131 and 132 may be referred to as the proximal joint part 131 and the distal joint part 132 according to the order of protruding out of the end of the tube 11.

Meanwhile, the structure and the number of joint parts 131 and 132 of the surgical robot 13 are not limited hereto.

As shown in FIG. 1, the surgical robot 13 may individually drive the proximal joint part 131 and the distal joint part 132 according to the drive input of the user.

For example, the surgical robot 13 may be not only articulated and driven, but also translated and driven in forward and backward directions according to the direction in which the end of the tube 11 is directed. Such being articulated and driven and being translated described above may be performed manually by the user, or may be performed automatically by a remote master mechanism.

The endoscopy camera 12 may capture the surgical robot 13 protruding out of the end of the tube 11. The surgical robot 13 being driven may be checked through the image captured by the endoscopy camera 12.

The driver 16 may include an actuator configured to control the surgical robot 13 to be articulated and driven and/or to be translated. As shown in FIG. 1, when the surgical robot 13 has two joint parts 131 and 132, the driver 16 may include a proximal drive part 161 configured to drive the proximal joint part 131 and a distal drive part 162 configured to drive the distal joint part 132.

The drive input part 15 may transmit a drive input signal received from the user to the controller 14. For example, the drive input signal may include angle values $\theta 1$ and $\theta 2$ at which the proximal joint part 131 and the distal joint part 132 are respectively bent or extended.

The controller 14 may control the movement of the surgical robot 13 through the drive of the driver 16 based on the drive input of the user. The controller 14 may compensate for the hysteresis of the surgical robot based on the drive input and the real-time image captured by the endoscopy camera 12.

For example, the controller 14 may include at least one processor 141 and a memory 142. The processor 141 may execute functions and instructions to determine a drive error of the surgical robot through the real-time image captured by the endoscopy camera 12 and compensate for the drive input through the drive error.

The memory 142 stores information, the functions, and the instructions for determining and compensating for the hysteresis of the surgical robot. The memory 142 may include a computer-readable storage medium or a computer-readable storage device.

Referring to FIGS. 3 and 4, the controller 14 may execute instructions based on the information stored in the memory 142 to perform the following functions.

For example, the controller 14 may include a preprocessor 143 configured to preprocess a real-time image 23 and an actual image 22 captured by the endoscopy camera 12, a hysteresis evaluation model 144 configured to determine the drive error of the surgical robot through the real-time image, an index part 145 for a similarity search through the real-time image, and a drive compensator 146 configured to compensate for the drive input based on the drive error. Here, the preprocessor 143, the hysteresis evaluation model 144, the index part 145, and the drive compensator 146 may refer to a set of functions performed using the processor 141 and the memory 142 described above, and are not necessarily physically separated from each other. Herein, the functions performed by the preprocessor 143, the hysteresis evaluation model 144, the index part 145, and the drive compensator 146 may be construed as the functions performed by the controller 14.

The hysteresis evaluation model 144 may extract feature vectors to effectively evaluate similarities between the actual image of the surgical robot 13 captured by the endoscopy camera 12 and images rendered by driving a virtual surgical robot 13 on a simulation that models the surgical robot 13 based on a kinematic model (hereinafter, the rendered images).

Here, a rendered image refers to an image captured by a virtual camera that is placed at a set position and angle relatively from the proximal joint part 131 of the surgical robot 13 and has a set field of view. Here, the set position and angle may be set equal to the relative positions and angles of the surgical robot 13 and the endoscopy camera 12 to be actually used in the process of generating a hysteresis evaluation model. In addition, the set field of view may be set equal to the field of view of the endoscopy camera 12 to be actually used in the process of generating a hysteresis evaluation model. For example, the rendered images may be extracted from a screen output by executing a modeling file created in the same manner as the surgical robot 13 manufactured with a three-dimensional design program. As another example, the surgical robot 13 may be imaged by an equation derived based on a kinetic model of the surgical robot 13.

For example, the controller 14 may include training data and a machine learning algorithm trained by supervised learning. The training data may include previously rendered images and a set of respective drive displacements, input on the simulation, corresponding to the respective images, and may also be referred to as a rendered image data set 147.

For example, the training data may further include actual images, and a set of values of drive displacements of the respective actual images.

For example, the image data set 147 may be rendered on the simulation that models the surgical robot based on the kinetic model based on a state in which the relative positions and angles of the endoscopy camera 12 and the proximal joint part 131 are fixed. Meanwhile, as another example, in the case of changing the relative position and angle of the endoscopy camera 12 to be actually used in the process of generating a hysteresis evaluation model, the image data set 147 may be generated while changing the relative positions and angles of the endoscopy camera 12 and the proximal joint part 131.

For example, the hysteresis evaluation model 144 may include a first neural network model 1441 configured to receive a previously rendered image of the surgical robot 13 and output a first feature vector having a plurality of dimensions, a second neural network model 1442 configured to receive an actual image of the surgical robot 13 and output a second feature vector, and a supervised learning model 1443 configured to train the first neural network model 1441 and the second neural network model 1442 by supervised learning, such that differences in relative magnitudes of respective drive displacements (drive inputs) of rendered images 21 and an actual image 22 are proportional to a difference in relative magnitudes between the first feature vector and the second feature vector. For example, the number of dimensions of the first feature vector and the number of dimensions of the second feature vector may be the same.

The function of the controller 14 and the method of compensating for the drive error of the surgical robot 13 through the hysteresis evaluation model 144 will be described in detail later with reference to FIGS. 6 to 12.

Figure 6:
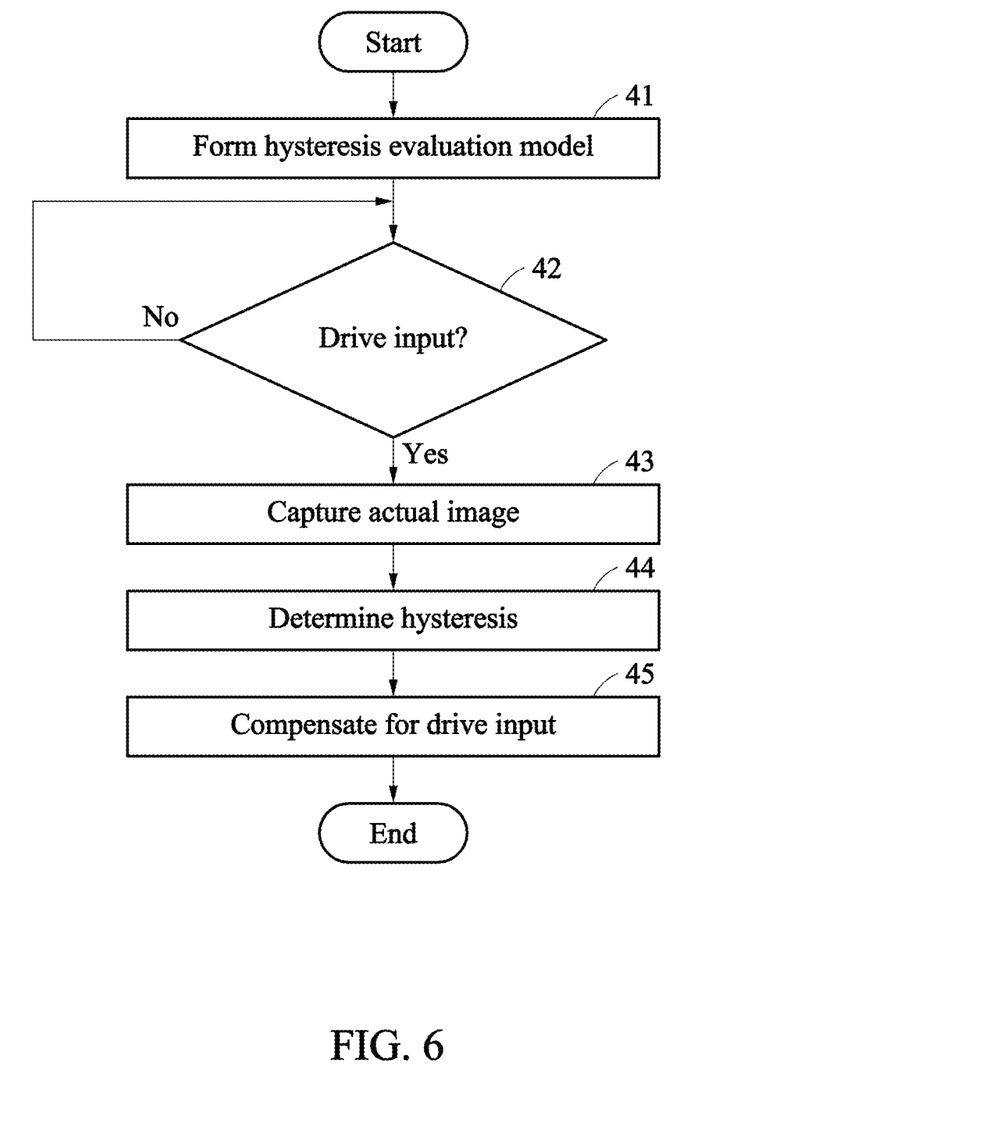
FIG. 6 is a flowchart illustrating a method of compensating for a hysteresis of a surgical robot according to an example embodiment.
Figure 7:
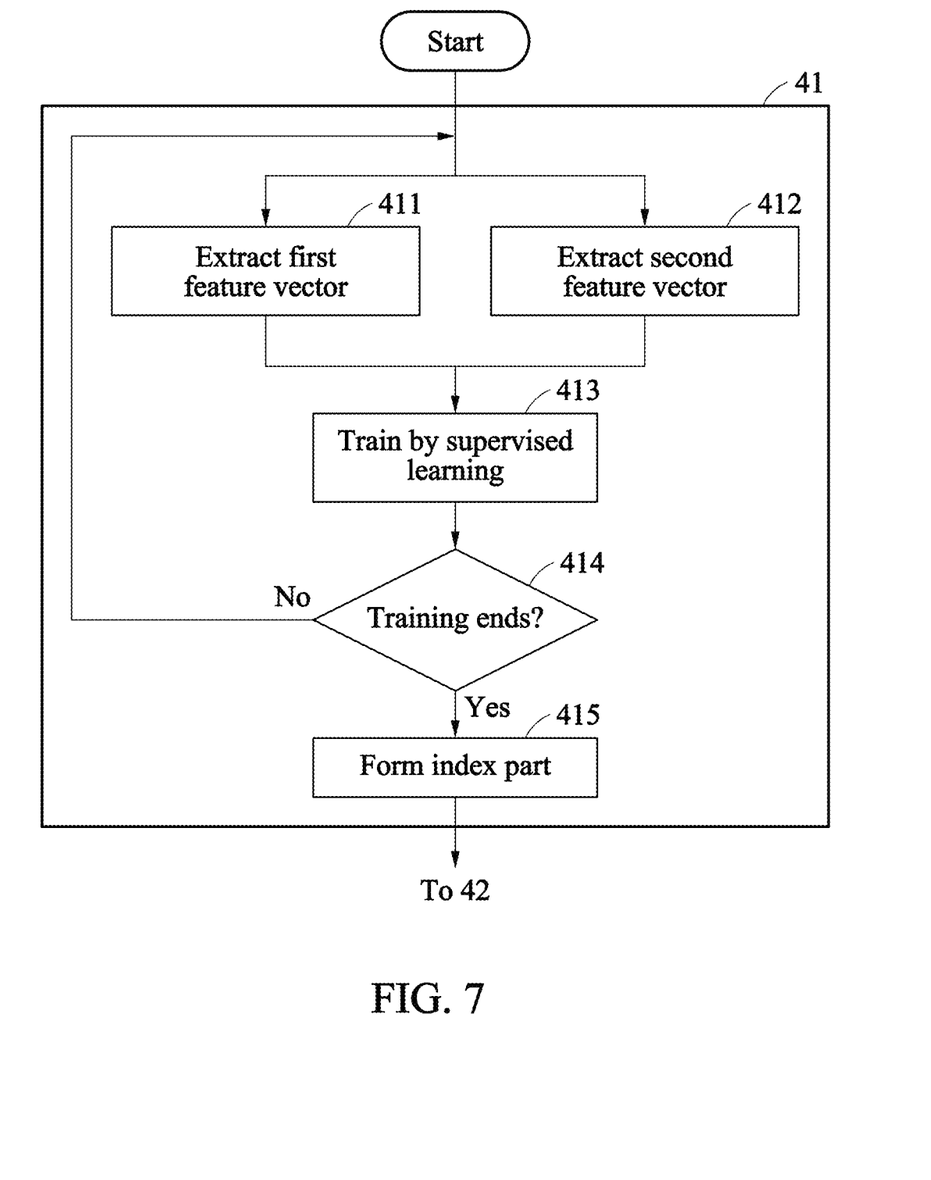
FIG. 7 is a flowchart illustrating an operation of generating a hysteresis evaluation model according to an example embodiment.
Figure 8:
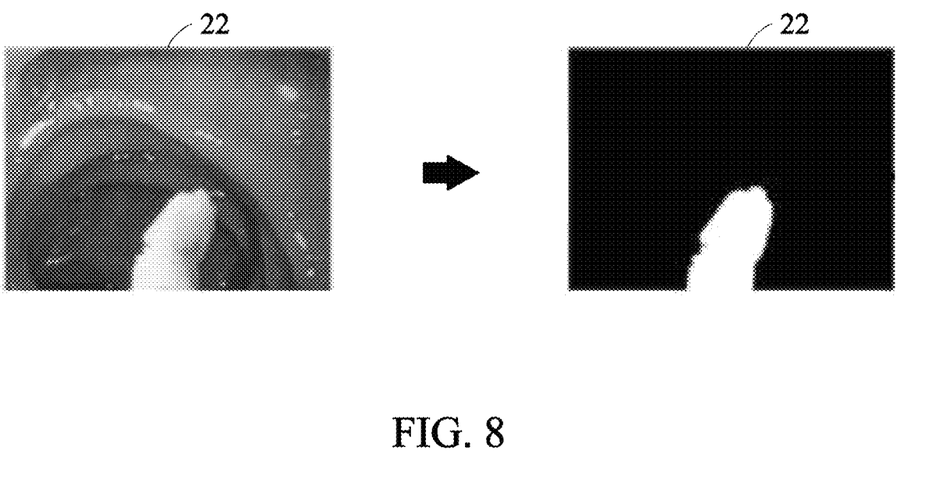
FIG. 8 illustrates an example of preprocessing an actual image captured by an endoscopy camera according to an example embodiment.
Figure 9:
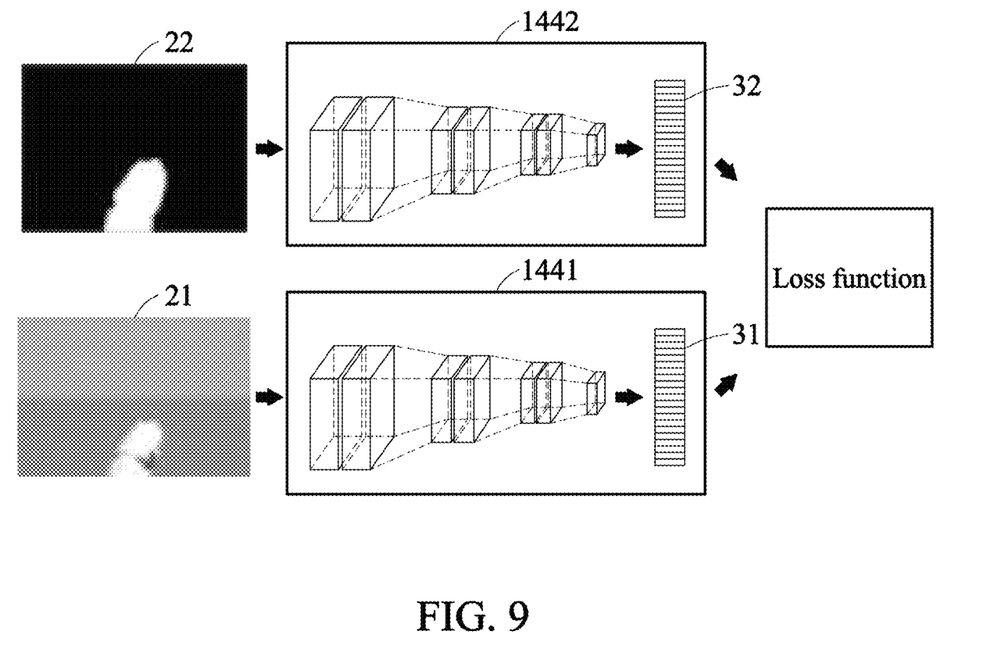
FIG. 9 illustrates a process of training two neural network models in an operation of generating a hysteresis evaluation model according to an example embodiment.
Figure 10:
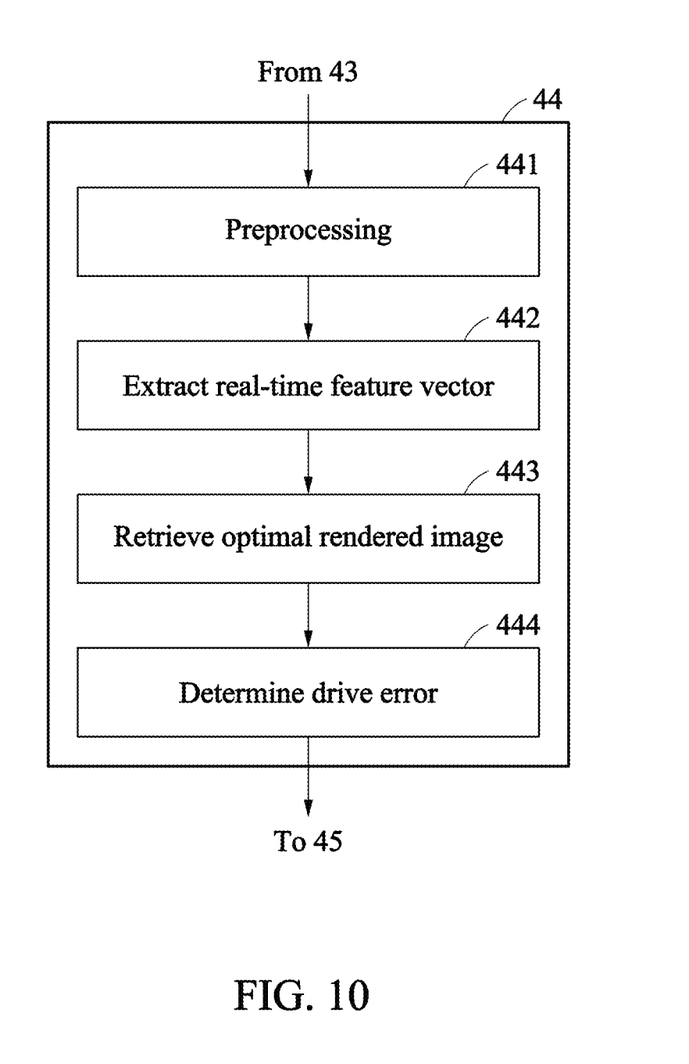
FIG. 10 is a flowchart illustrating an operation of determining hysteresis according to an example embodiment.
Figure 11:
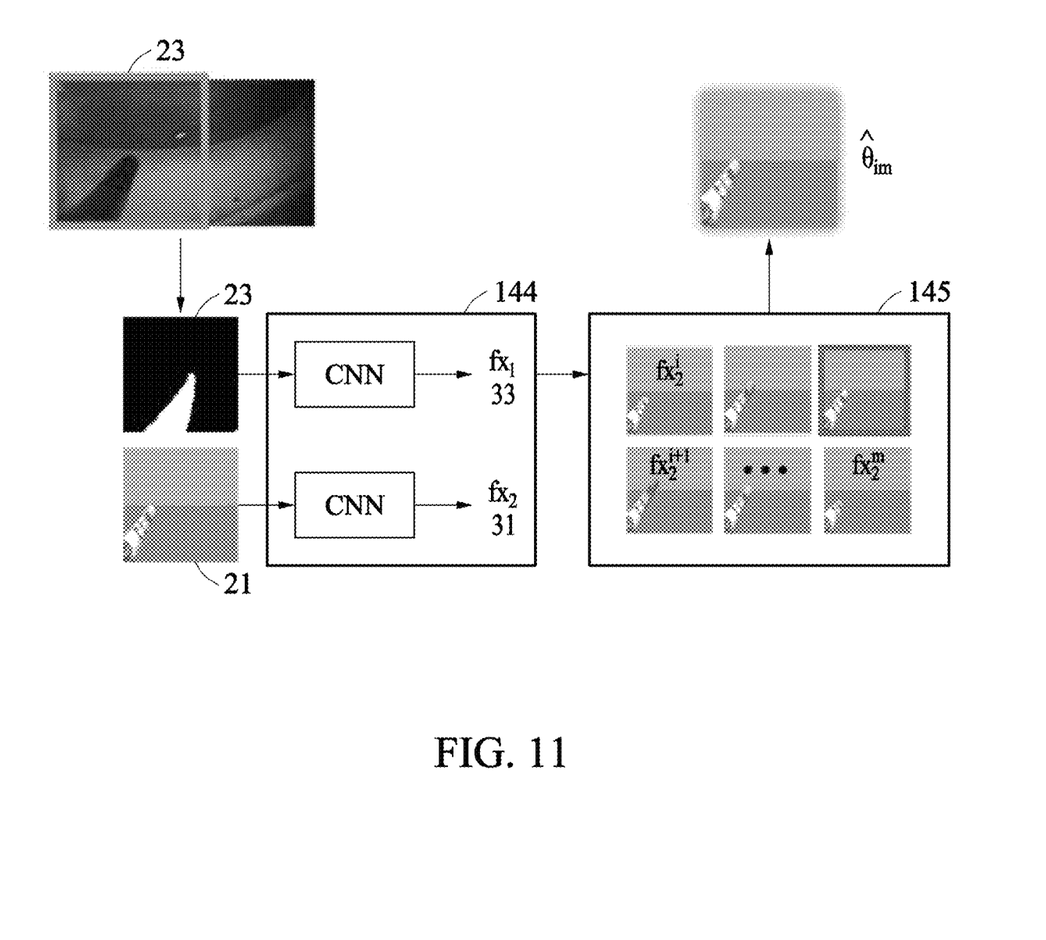
FIG. 11 illustrates a process of retrieving a rendered image similar to a real-time image through an operation of determining hysteresis according to an example embodiment.
Figure 12:
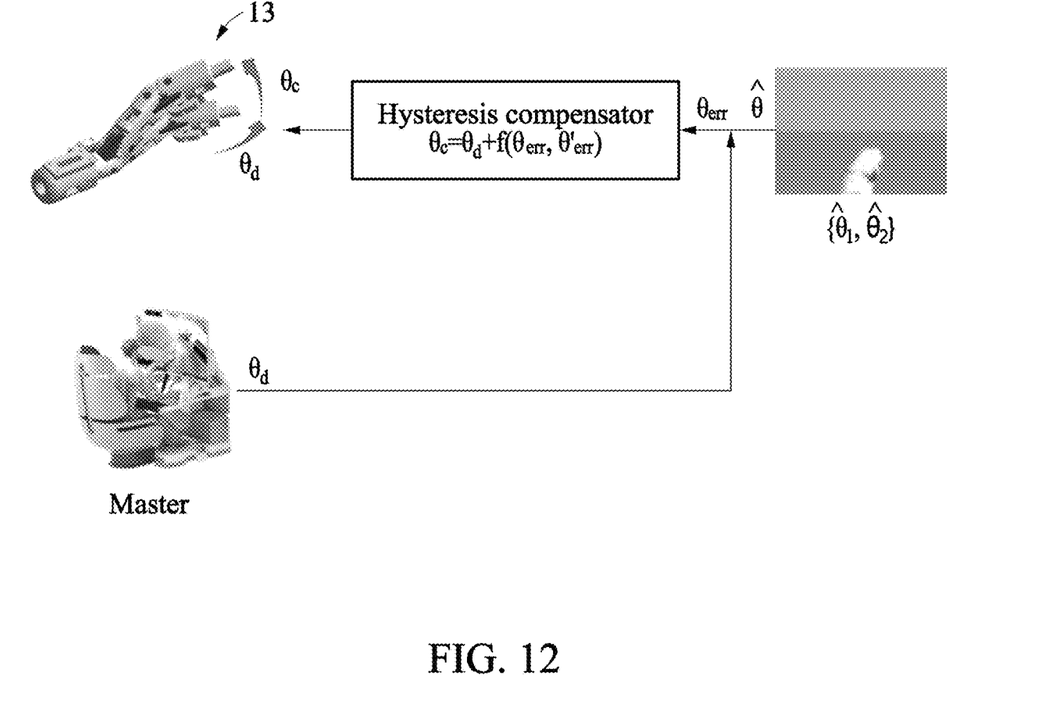
FIG. 12 illustrates a process of compensating for a drive error according to a drive input of a user in an operation of compensating for the drive error according to an example embodiment.

FIG. 6 is a flowchart illustrating a method of compensating for a hysteresis of a surgical robot according to an example embodiment, FIG. 7 is a flowchart illustrating an operation of generating a hysteresis evaluation model according to an example embodiment, FIG. 8 illustrates an example of preprocessing an actual image captured by an endoscopy camera according to an example embodiment, FIG. 9 illustrates a process of training two neural network models in the operation of generating a hysteresis evaluation model according to an example embodiment, FIG. 10 is a flowchart illustrating an operation of determining hysteresis according to an example embodiment, FIG. 11 illustrates a process of retrieving a rendered image similar to a real-time image through the operation of determining hysteresis according to an example embodiment, and FIG. 12 illustrates a process of compensating for a drive error according to a drive input of a user in an operation of compensating for the drive error according to an example embodiment.

Referring to FIGS. 6 to 12, a method of compensating for hysteresis may include operation 41 of forming a hysteresis evaluation model, operation 42 of receiving a drive input, operation 43 of capturing a real-time image, operation 44 of determining hysteresis, and operation 45 of compensating for the drive input.

Operation 41 of forming a hysteresis evaluation model may be an operation of generating and training an artificial neural network model configured to evaluate similarities between the actual image 22 of the surgical robot 13 and the images 21 rendered by driving the surgical robot 13 on a simulation.

For example, operation 41 of forming a hysteresis evaluation model may include operation 411 of extracting a first feature vector 31 by inputting the images 21 rendered by driving the surgical robot 13 on the simulation into the first neural network model 1441, operation 412 of extracting a second feature vector 32 by inputting the actual image 22 of the surgical robot 13 driven according to the drive input into the second neural network model 1442, operation 413 of training the first neural network model 1441 and the second neural network model 1442 by supervised learning based on differences in relative magnitudes of respective drive displacements of the rendered images 21 and the actual image 22 and on a difference in relative magnitudes between the first feature vector 31 and the second feature vector 32, operation 414 of verifying whether to end training, and operation 415 of forming an index part configured to store values of the first feature vector 31 extracted for the respective rendered images 21.

Each of the first neural network model 1441 and the second neural network model 1442 may include an artificial neural network model. For example, the first neural network model 1441 and the second neural network model 1442 may each include a convolutional neural network (CNN) structure.

For example, the first neural network model 1441 and the second neural network model 1442 may each include one or more convolutional layers, pooling layers, and fully connected layers, and the two neural network models 1441 and 1442 may have the same hierarchical structure.

For example, when the surgical robot 13 includes two or more joint parts, as shown in FIG. 1, the hysteresis evaluation model 144 may be generated as at least two different models, for each interval of the drive displacement of any one of the two or more joint parts. According to the above structure, it is possible to alleviate the problem that the conditions causing hysteresis are formed differently according to a drive interval of the proximal joint part 131, thereby generating a more accurate hysteresis evaluation model and efficiently improving the learning speed. For example, the hysteresis evaluation model 144 may be generated as at least two different models, separately for each interval of the drive displacement of the proximal joint part 131.

In operation 411 of extracting the first feature vector 31, the rendered images 21 may be input into the first neural network model 1441, processed by the plurality of convolutional layers and pooling layers, input into the fully connected layers, and extracted as the values of the first feature vector 31 having a plurality of dimensions.

In operation 412 of extracting the second feature vector 32, the actual image 22 of the surgical robot 13 may be input into the second neural network model 1442, processed by the plurality of convolutional layers and pooling layers, input into the fully connected layers formed of multi-layer perceptron (MLP), and extracted as the values of the second feature vector 32 having a plurality of dimensions.

For example, the actual image 22 of the surgical robot 13 and a data set of drive displacements actually measured for respective actual images 22 may be used as training data for the two neural network models 1441 and 1442, together with the previously rendered image data set 147.

The first feature vector 31 and the second feature vector 32 output respectively from the first neural network model 1441 and the second neural network model 1442 may have the same number of dimensions.

For example, operation 411 of extracting the first feature vector 31 may include a preprocessing operation of separating and removing a background image except for the surgical robot 13 from the actual image 22.

For example, in the preprocessing operation, the controller 14 may extract only the shape of the surgical robot 13 using an image segmentation technique to remove a complex organ image background from the actual image 22.

For example, the controller 14 may separate the area of the surgical robot 13 and the background in the actual image 22 with binary values.

Operation 413 of training by supervised learning may be a process of training the first neural network model 1441 and the second neural network model 1442 through a backpropagation algorithm such that the difference between the first feature vector 31 and the second feature vector 32 decreases as the respective drive displacements (drive inputs) of the rendered images 21 and the actual image 22 are similar to each other.

In operation 413 of training by supervised learning, the controller 14 may define the distance d between the first feature vector 31 and the second feature vector 32 as a norm between the two vectors 31 and 32. This means the smaller the distance d, the smaller the difference between the respective drive displacements of the rendered images 21 and the actual image 22.

$$d(x_1 \circ x_2)^2 = \Sigma_j |f_{x_1} - f_{x_2}|^2 \quad \text{[Equation 1]}$$

($x_1$: rendered image, $x_2$: actual image, $F_{x1}$: first feature vector, $F_{x2}$: second feature vector)

For example, the controller 14 may set a loss function for the similarity using the concept of binary cross-entropy, and train the first neural network model 1441 and the second neural network model 1442 with the value of the loss function using gradient descent.

For example, the loss function may be defined as in Equation 2 below. However, the loss function may also be set in a different manner.

$$L(x_1, x_2, y) = \frac{1}{2N} \sum_{n=1}^{N} [y \times d(x_1 \circ x_2)^2 + (1-y)\max(1 - d(x_1 \circ x_2), 0)^2] \quad \text{[Equation 2]}$$

In operation 414 of verifying whether to end training, whether the first neural network model 1441 and the second neural network model 1442 are sufficiently trained may be determined.

In operation 414 of verifying whether to end training, the controller 14 may train the first neural network model 1441 and the second neural network model 1442 until the value of a set loss function output when the training data are input into the first neural network model 1441 and the second neural network model 1442 is lower than a set value.

In response to the determination that training is sufficiently performed in operation 414 of verifying whether to end training, operation 415 of forming an index part may be performed.

In operation 415 of forming an index part, the controller 14 may store, in an indexable data structure, the first feature vector 31 extracted from each of the rendered images 21 used for training.

For example, the controller 14 may store data of first feature vectors 31 extracted respectively for the rendered images 21 as the index part 145 with a binary tree structure having the same number of dimensions as the first feature vector 31. For example, the data structure of the index part 145 may be a K-dimensional (K-D) tree structure.

When the K-D tree structure is used, the amount of hysteresis may be verified at a level the same as the time required to acquire images actually through the endoscopy camera 12 or at a faster level. Meanwhile, the index part 145 may be implemented by those skilled in the art using various data structures or search algorithms.

In operation 42 of receiving a drive input, the controller 14 may verify whether a drive input is applied by the drive input part 15. In response to the determination that a drive input is applied, operation 43 of capturing a real-time image may be performed. Meanwhile, operation 42 of receiving a drive input may also be performed before operation 43 of capturing a real-time image or at the same time with operation 43.

In operation 43 of capturing a real-time image, the controller 14 may acquire the real-time image 23 of the surgical robot 13 according to the drive input through the endoscopy camera 12.

In operation 44 of determining hysteresis, the controller 14 may measure a drive angle of the surgical robot 13 based on the real-time image 23, and calculate a degree of hysteresis, that is, a drive error, of the surgical robot 13 by comparing the measured drive angle to an actually input drive input. Operation 44 may be construed as an operation of calculating a difference between the drive input and the measured drive angle.

For example, operation 44 of determining hysteresis may include operation 441 of preprocessing the real-time image, operation 442 of extracting a real-time feature vector 33 by inputting the real-time image 23 of the surgical robot 13 into the second neural network model 1442 through the endoscopy camera 12, operation 443 of retrieving a rendered image having a first feature vector 31 most similar to the real-time feature vector 33, and operation 444 of determining a drive error based on a difference between the drive input and a drive displacement of the rendered image 21.

In operation 441 of preprocessing, the controller 14 may extract only the shape of the surgical robot 13 using an image segmentation technique to remove a complex organ image background from the real-time image 23. Meanwhile, to distinguish between the preprocessing operation of operation 411 and the preprocessing operation of operation 441, they may also be referred to as "first preprocessing operation" and "second preprocessing operation".

For example, the controller 14 may separate the area of the surgical robot 13 and the background in the real-time image 23 with binary values.

For example, operation 441 of preprocessing may further include an operation of adjusting a scale of the real-time image. By this operation, even if the distance from the camera 12 to the proximal joint part 131 changes, the existing hysteresis evaluation model may be utilized without a need of newly generating a hysteresis evaluation model. In other words, it is possible to measure drive angles of the surgical robot 13 moved forward and backward various distances from the tube 11, based on a hysteresis evaluation model generated based on the surgical robot 13 moved forward a predetermined distance.

In operation 441, the controller 14 may detect the distance from the camera 12 to the proximal joint part 131 on the real-time image 23. By enlarging the real-time image as the detected distance increases, subsequent operation 442, and the like may be performed using the enlarged real-time image. For example, the enlargement ratio may be determined based on a value obtained by dividing the detected distance by the distance from the camera 12 to the proximal joint part 131.

In operation 442 of extracting a real-time feature vector 33, the controller 14 may extract the real-time feature vector 33 by inputting the real-time image 23 of the surgical robot 13 driven according to the drive input into the trained second neural network model 1442.

In operation 443 of retrieving a rendered image having a first feature vector 33 most similar to the real-time feature vector 33, the controller 14 may retrieve a rendered image 21 most similar to the real-time image 23.

For example, the controller 14 may retrieve a first feature vector 31 at the shortest distance from the real-time feature vector 33, among the first feature vectors 31 extracted respectively for the rendered images 21, and retrieve a rendered image 21 having the corresponding first feature vector 31. The image retrieved as described above may also be referred to as an optimal rendered image 21.

For example, the controller 14 may use the index part 145 configured in a multi-dimensional binary tree to find the first feature vector 31 at the shortest distance from the real-time feature vector 33.

In operation 444 of determining a drive error, the controller 14 may determine a drive error based on a difference between the drive displacement of the optimal rendered image 21 and the drive input that is input in real time.

In operation 45 of compensating for a drive input, the controller 14 may compensate for a drive input based on the determined drive error through the drive compensator 146.

The drive compensator 146 may drive the driver 16 by compensating for the drive input such that the drive error converges to "0" based on the drive input and the drive error detected accordingly.

The drive compensator 146 may compensate for the drive input based on the size of the drive error. For example, the drive compensator 146 may compensate for the drive input with feedback control based on the size of the drive error.

For example, the drive compensator 146 may compensate for the drive input based on a compensation function including a combination of proportional control, integral control, and differential control of the drive error as expressed in Equation 3 below. Meanwhile, the following compensation function is merely an example. The compensation function may also be set in a different manner.

$$f(\theta_{err}, \dot{\theta}_{err}) = K_p \theta_{err} + K_d \dot{\theta}_{err} + K_i \int \theta_{err} dt \qquad \text{[Equation 3]}$$

Thereafter, the controller 14 may compensate for the drive input of the surgical robot 13 by applying a compensation value output from the compensation function to the existing drive input.

The units described herein may be implemented using a hardware component, a software component and/or a combination thereof. A processing device may be implemented using one or more general-purpose or special-purpose computers, such as, for example, a processor, a controller and an arithmetic logic unit (ALU), a DSP, a microcomputer, an FPGA, a programmable logic unit (PLU), a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or uniformly instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network-coupled computer systems so that the software is stored and executed in a distributed fashion. The software and data may be stored by one or more non-transitory computer-readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher-level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

The invention claimed is:

1. A method of determining hysteresis of a surgical robot according to a drive input, the method comprising:
   generating a hysteresis evaluation model for the surgical robot based on similarities between (i) an actual image of the surgical robot and (ii) images rendered by driving a virtual surgical robot on a simulation that models the surgical robot based on a kinetic model;
   capturing a real-time image of the surgical robot driven according to a drive input; and
   measuring a drive angle of the surgical robot by comparing the real-time image to a previously rendered image data set of the surgical robot, and calculating a difference between the drive input and the measured drive angle.

2. The method of claim 1, wherein the generating of the hysteresis evaluation model comprises:
   extracting a first feature vector by inputting rendered image data, which are a set of the rendered images, into a first neural network model;
   extracting a second feature vector by inputting actual image data of the surgical robot driven according to a drive input into a second neural network model; and
   training the first neural network model and the second neural network model by supervised learning, based on a difference in relative magnitudes of respective drive inputs of the rendered images and the actual image and on a difference in relative magnitudes between the first feature vector and the second feature vector.

3. The method of claim 2, wherein the first feature vector and the second feature vector have the same number of dimensions, and
   the training comprises training the first neural network model and the second neural network model such that a norm size between the first feature vector and the second feature vector decreases as the respective drive inputs of the rendered images and the actual image are more similar to each other.

4. The method of claim 3, wherein the surgical robot comprises a proximal joint part and a distal joint part that have different rotation axes are articulated and driven,
   the drive inputs comprise a drive angle displacement of the proximal joint part and a drive angle displacement of the distal joint part, and
   the generating of the hysteresis evaluation model comprises generating at least two hysteresis evaluation models, for each interval of the drive angle displacement of any one of the proximal joint part and the distal joint part.

5. The method of claim 4, wherein the generating of the hysteresis evaluation model comprises generating at least two hysteresis evaluation models, for each interval of the drive angle displacement of the proximal joint part.

6. The method of claim 2, wherein the generating of the hysteresis evaluation model further comprises preprocessing the actual image by separating and removing a background image except for the surgical robot from the actual image.

7. The method of claim 2, wherein the calculating of the difference comprises:
   extracting a real-time feature vector by inputting the real-time image into the second neural network model;
   retrieving a rendered image having the first feature vector most similar to the real-time feature vector; and
   determining the measured drive angle based on a drive input of the retrieved rendered image.

8. The method of claim 7, wherein the retrieving of the rendered image comprises indexing using a binary tree structure having the number of dimensions the same as the number of dimensions of the first feature vector.

9. The method of claim 8, wherein the calculating of the difference further comprises preprocessing the real-time image by separating and removing a background image except for the surgical robot from the real-time image.

10. The method of claim 9, wherein the preprocessing further comprises adjusting a scale of the real-time image based on a distance from a camera capturing the real-time image of the surgical robot to a proximal joint part of the surgical robot.

11. A method of compensating for hysteresis of a surgical robot according to a drive input, the method comprising:
    generating a hysteresis evaluation model for the surgical robot based on similarities between (i) an actual image of the surgical robot and (ii) images rendered by driving a virtual surgical robot on a simulation that models the surgical robot based on a kinetic model;
    capturing a real-time image of the surgical robot driven according to a drive input;
    measuring a drive angle of the surgical robot by comparing the real-time image to a previously rendered image data set of the surgical robot, and determining hysteresis of the surgical robot by calculating a difference between the drive input and the measured drive angle; and
    compensating for the drive input based on the determined hysteresis.

12. The method of claim 11, wherein the compensating comprises compensating for the drive input with feedback control based on the difference between the drive input and the measured drive angle.

13. An endoscopic surgical apparatus, comprising:
    a tube;
    a surgical robot received in the tube, the surgical robot having a drive shaft with one or more degrees of freedom;
    an endoscopy camera configured to capture a actual image of the surgical robot at an end of the tube;
    a driver configured to drive the surgical robot;
    a controller configured to control the drive of the surgical robot by controlling the driver; and
    a drive input part configured to receive a drive input from a user,
    wherein the controller comprises a hysteresis evaluation model, wherein the hysteresis evaluation model is generated based on similarities between the actual image of the surgical robot and images rendered by driving a virtual surgical robot on a simulation that models the surgical robot based on a kinetic model,
    wherein the controller comprises at least one processor configured to compensate for hysteresis of the surgical robot based on the drive input and a real-time image captured by the endoscopy camera.

14. The endoscopic surgical apparatus of claim 13, wherein the hysteresis evaluation model for the surgical robot comprises:
   a first neural network model configured to receive the rendered images and output a first feature vector of a plurality of dimensions;
   a second neural network model configured to receive the actual image of the surgical robot and output a second feature vector having the same number of dimensions as the first feature vector; and
   a supervised learning model configured to train the first neural network model and the second neural network model by supervised learning, such that a difference in relative magnitudes of respective drive inputs of the rendered images and the actual image is proportional to a difference in relative magnitudes between the first feature vector and the second feature vector.

15. The endoscopic surgical apparatus of claim 14, wherein the hysteresis evaluation model for the surgical robot further comprises:
   an index part configured to store first feature vectors extracted respectively for the rendered images in a binary tree structure having the number of dimensions the same as the number of dimensions of the first feature vector.

16. The endoscopic surgical apparatus of claim 14, wherein the surgical robot comprises a proximal joint part and a distal joint part that have different rotation axes are articulated and driven,
   the drive inputs comprise a drive angle displacement of the proximal joint part and a drive angle displacement of the distal joint part, and
   the hysteresis evaluation model is generated as at least two different models, for each interval of a drive angle displacement of any one of the proximal joint part and the distal joint part.

17. The endoscopic surgical apparatus of claim 14, wherein the controller is configured to extract a real-time feature vector by inputting a real-time image of the surgical robot into the second neural network model, and determine a drive error according to the drive input based on a rendered image having the first feature vector most similar to the real-time feature vector.

18. The endoscopic surgical apparatus of claim 17, wherein the controller further comprises a drive compensator configured to compensate for the drive of the driver based on a size of the drive error evaluated according to the drive input.

19. The endoscopic surgical apparatus of claim 18, wherein the drive compensator is configured to compensate for the drive input with feedback control based on the size of the drive error.

* * * * *